United States Patent
Foerster et al.

(10) Patent No.: US 10,653,608 B2
(45) Date of Patent: May 19, 2020

(54) AGENTS AND METHODS FOR THE TEMPORARY SHAPING OF KERATIN-CONTAINING FIBERS

(71) Applicant: Henkel AG & Co. KGaA, Duesseldorf (DE)

(72) Inventors: Thomas Foerster, Duesseldorf (DE); Rolf Bayersdoerfer, Hamburg (DE); Thorsten Knappe, Schenefeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 60 days.

(21) Appl. No.: 15/531,491

(22) PCT Filed: Nov. 2, 2015

(86) PCT No.: PCT/EP2015/075393
§ 371 (c)(1),
(2) Date: May 30, 2017

(87) PCT Pub. No.: WO2016/091469
PCT Pub. Date: Jun. 16, 2016

(65) Prior Publication Data
US 2017/0258699 A1    Sep. 14, 2017

(30) Foreign Application Priority Data
Dec. 10, 2014   (DE) .................. 10 2014 225 429

(51) Int. Cl.
*A61K 8/81* (2006.01)
*A61K 8/34* (2006.01)
*A61Q 5/06* (2006.01)

(52) U.S. Cl.
CPC .............. *A61K 8/8158* (2013.01); *A61K 8/34* (2013.01); *A61Q 5/06* (2013.01); *A61K 2800/87* (2013.01)

(58) Field of Classification Search
CPC .......... A61K 8/34; A61K 8/8158; A61Q 5/06
See application file for complete search history.

(56) References Cited

U.S. PATENT DOCUMENTS

| | | |
|---|---|---|
| 3,372,840 A | 3/1968 | Kelley |
| 3,869,970 A | 3/1975 | Eagle |
| 4,192,861 A | 3/1980 | Micchelli et al. |
| 2003/0141378 A1 | 7/2003 | Raehse et al. |
| 2004/0146471 A1 | 7/2004 | Gaenger et al. |
| 2004/0224873 A1 | 11/2004 | Raehse et al. |
| 2005/0207992 A1 | 9/2005 | Detert et al. |
| 2013/0018333 A1 | 1/2013 | Thomason et al. |
| 2017/0273424 A1* | 9/2017 | Mueller ............ A61Q 5/10 |

FOREIGN PATENT DOCUMENTS

| | | |
|---|---|---|
| DE | 102011086559 A1 | 5/2013 |
| WO | 9303705 A1 | 3/1993 |

OTHER PUBLICATIONS

Amphomer(R) LV-71 data sheet, edicted Dec. 19, 2018 and accessed via https://cosmetics.specialchem.com/product/i-nouryon-amphomer-lv-71 on Feb. 21, 2019.*
EPO, International Search Report and Written Opinion issued in International Application PCT/EP2015/075393, dated Feb. 8, 2016.

* cited by examiner

*Primary Examiner* — Kortney L. Klinkel
(74) *Attorney, Agent, or Firm* — Lorenz & Kopf, LLP

(57) ABSTRACT

The invention relates to a cosmetic product, comprising a) a cosmetic preparation, containing, in relation to its total weight, a1) about 45 to about 98 wt. % of at least one polar solvent; a2) about 0.5 to about 15 wt. % of at least one copolymer from the monomers i) n-tert-octylacrylamide, ii) acrylic acid, iii) tert-butylamino ethyl methacrylate, iv) and optionally other monomers; b) a device for flash evaporation of the cosmetic preparation a), and to a method using corresponding products and to the use of the cosmetic preparation a) as process material in a device for flash evaporation.

20 Claims, No Drawings

AGENTS AND METHODS FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2015/075393, filed Nov. 2, 2015, which was published under PCT Article 21(2) and which claims priority to German Application No. 10 2014 225 429.9, filed Dec. 10, 2014, which are all hereby incorporated in their entirety by reference.

TECHNICAL FIELD

The application relates to the technical field of the temporary shaping of keratinic fibers, in particular human hair. The invention pertains to specific cosmetic hair formulations which are suitable for application to keratinic fibers using a flash evaporation method. Furthermore, the use of these cosmetic hair formulations in devices for flash evaporation and methods for the temporary shaping of keratinic fibers also constitute objects of the present application.

BACKGROUND

A good-looking hairstyle is now generally seen as being an essential part of a groomed appearance. Current fashion trends are dictating more and more hairstyles which are considered to be chic but which can only be achieved with many hair types by using firming substances, or they have to be maintained for a long period of time of up to several days. Thus, hair treatment agents, which provide the hair with a permanent or temporary shape, play an important role. While permanent shaping modifies the chemical structure of the keratinic fibers by reduction and oxidation, modifications of that type to the chemical structure do not take place with temporary reshaping. Appropriate agents for temporary shaping usually contain synthetic polymers and/or waxes as the firming substance.

The most important property of an agent for temporary shaping of keratinic fibers, herein also termed styling agents, is that the fibers when treated when in their newly remodelled form—i.e. the fibers have been styled—are provided with as strong a hold as possible. When the keratinic fibers are human hair, this is also known as a strong styling hold or a strong hold for the styling agent. The styling hold is essentially determined by the type and quantity of the firming substances used, but the other components of the styling agent and the form of application may also have an influence.

In the field of the temporary shaping of keratinic fibers, spray application of appropriate cosmetic preparations is of particular importance, wherein as a rule, the preparations are applied using pump sprays or aerosol sprays. In this regard, the cosmetic preparations are packaged in a dispensing device from which they are sprayed, either by employing mechanical force, or with the aid of a propellant through a valve. Both methods have obvious disadvantages. While pump sprays are not usually suitable for the prolonged, uniform application of cosmetic hair preparations, aerosol sprays are based on the use of propellants or propellant gases which on the one hand do not have any cosmetic action and on the other hand, can risk harming the consumer if handled ineptly.

In the light of this, there is a need for alternative methods for spraying cosmetic hair preparations. Flash evaporation has proved to be such an alternative spraying method. In this method which, for example, has been described in international patent application WO 2001/83071 A1 (Henkel), a fluid or pasty composition containing a solvent is heated in a sealed chamber to a temperature which is above the boiling point of the solvent, whereupon a positive pressure is produced in the composition. Upon release (reduction) of the pressure, the liquid evaporates and can then, for example, be sprayed using a suitable nozzle.

Although flash evaporation is thus in principle suitable for spray application of cosmetic hair preparations, at the same time, however, not all cosmetic hair preparations can be sprayed using a flash evaporation method. This is attributable on the one hand to the cosmetic preparation having to be heated for flash evaporation, and on the other hand to the characteristics of the spray mist produced by the flash evaporation, for example the droplet size and droplet density produced in the spray mist.

BRIEF SUMMARY

A cosmetic product is provided herein. The cosmetic product includes a cosmetic preparation. The cosmetic preparation includes, with respect to its total weight, about 45% to about 98% by weight of at least one polar solvent. The cosmetic preparation further includes, with respect to its total weight, about 0.5% to about 15% by weight of at least one copolymer selected from the monomers i) N-tert-octylacrylamide, ii) acrylic acid, iii) tert-butylaminoethylmethacrylate, and iv) optionally, other monomers. The cosmetic product further includes a device for flash evaporation of the cosmetic preparation.

A cosmetic preparation is also provided herein. The cosmetic preparation includes, with respect to its total weight, about 45% to about 98% by weight of at least one polar solvent. The cosmetic preparation further includes, with respect to its total weight, about 0.5% to about 15% by weight of at least one copolymer selected from the monomers i) N-tert-octylacrylamide, ii) acrylic acid, iii) tert-butylaminoethylmethacrylate, and iv) optionally, other monomers. The cosmetic preparation is utilized as a material in a device for flash evaporation.

A method for for temporarily shaping keratinic fibers is also provided herein. The method includes applying a cosmetic preparation a) to the keratinic fibers using a device for flash evaporation. The cosmetic preparation includes, with respect to its total weight, about 45% to about 98% by weight of at least one polar solvent. The cosmetic preparation further includes, with respect to its total weight, about 0.5% to about 15% by weight of at least one copolymer selected from the monomers i) N-tert-octylacrylamide, ii) acrylic acid, iii) tert-butylaminoethylmethacrylate, and iv) optionally, other monomers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Thus, the aim as contemplated herein is to provide specific cosmetic hair preparations for temporary shaping of keratinic fibers which, because of its chemical and physical properties, are suitable for specific spray application using a device for flash evaporation. Furthermore, the preparations should be suitable for producing a strong hold after application using a flash evaporation method, in particular a strong, long-lasting hold, and a high volume effect. It has been shown that in order to achieve this aim, from the many known cosmetic hair polymeric preparations, in particular, solvent-containing preparations based on a copolymer of the monomers N-tert-octylacrylamide, acrylic acid and tert-butylaminoethylmethacrylate are suitable.

In a first aspect, then, the present disclosure provides a cosmetic product comprising
a) a cosmetic preparation containing, with respect to its total weight
   a1) about 45% to about 98% by weight of at least one polar solvent
   a2) about 0.5% to about 15% by weight of at least one copolymer selected from the monomers
      i) N-tert-octylacrylamide
      ii) acrylic acid
      iii) tert-butylaminoethylmethacrylate
      iv) as well as other monomers if appropriate
b) a device for flash evaporation of the cosmetic preparation a).

The cosmetic preparation a) is preferably liquid. The cosmetic preparation a) may be a solution or dispersion, for example an emulsion or suspension. Preferred cosmetic preparations a) are in the form of a solution or a suspension.

The cosmetic preparation as contemplated herein contains, as the first essential component, about 45% to about 98% by weight of at least one polar solvent a1). Preferred cosmetic products are wherein the proportion by weight of the polar solvent a1) with respect to the total weight of the cosmetic preparation a) is about 55% to about 92% by weight, preferably about 70% to about 90% by weight. Appropriate agents are distinguished by a good cosmetic effect at the same time as good applicability.

In order to improve the application properties of cosmetic preparations as contemplated herein and at the same time to minimize the thermal load on any substances or excipients during the flash evaporation procedure, it has been shown to be advantageous to use polar solvents a1) which have a boiling point (20° C., 1013 mbar) between about 50° C. and about 110° C., preferably between about 70° C. and about 105° C. In this regard, ethanol, isopropanol and water have been shown to be particularly suitable for use as the polar solvent a1).

Particularly preferred polar solvents a1) or solvent systems are
   polar solvents a1) comprising more than about 70% by weight, preferably more than about 75% by weight and in particular more than about 80% by weight of ethanol, respectively with respect to the total weight of the polar solvent;
   polar solvents a1) comprising, respectively with respect to the total weight of the polar solvent, more than about 80% by weight, preferably more than about 90% by weight and in particular more than about 95% by weight of a mixture of ethanol and water, wherein the ratio by weight of ethanol to water is preferably about 12:1 to about 4:1, preferably about 10:1 to about 6:1;
   polar solvents a1) comprising more than about 80% by weight, preferably more than about 88% by weight and in particular more than about 92% by weight of water, respectively with respect to the total weight of the polar solvent.

More particularly preferred cosmetic preparations are wherein the proportion of volatile components is a maximum of about 55% by weight. The group of these volatile components also includes the polar solvent ethanol. In other words, more particularly preferred cosmetic preparations are therefore wherein the proportion by weight of the ethanol in the total weight of the cosmetic preparation is a maximum of about 55% by weight, preferably about 10% to about 55% by weight, particularly preferably about 25% to about 55% by weight and in particular about 40% to about 55% by weight.

In a further preferred aspect, therefore, the present disclosure provides a cosmetic product comprising
a) a cosmetic preparation containing, with respect to its total weight
   a1) about 45% to about 98% by weight of at least one polar solvent, wherein the proportion by weight of the ethanol with respect to the total weight of the cosmetic preparation is a maximum of about 55% by weight, preferably about about 10% to about 55% by weight, particularly preferably about 25% to about 55% by weight and in particular about 40% to about 55% by weight;
   a2) about 0.5% to about 15% by weight of at least one copolymer selected from the monomers
      i) N-tert-octylacrylamide
      ii) acrylic acid
      iii) tert-butylaminoethylmethacrylate
      iv) as well as other monomers if appropriate;
b) a device for flash evaporation of the cosmetic preparation a), comprising
   b1) a container b1) which can be closed and opened by employing a valve
   b2) a heating device for heating a cosmetic preparation in the container b1)
   b3) a nozzle b3) for spraying the cosmetic preparation a).

A preferred combination of polar solvents a1) comprises water and ethanol, wherein
   the proportion by weight of water and ethanol with respect to the total weight of the polar solvent a1) is preferably at least about 60% by weight, preferably at least about 80% by weight, particularly preferably at least about 90% by weight and in particular at least about 95% by weight, and preferably furthermore
   the proportion by weight of water to ethanol is about 5:1 to about 1:5, preferably about 2:1 to about 1:2, and in particular about 5:4 to about 4:5.

In a further preferred aspect, the present disclosure therefore provides a cosmetic product comprising
a) a cosmetic preparation containing, with respect to its total weight
   a1) about 45% to about 98% by weight of at least one polar solvent, wherein
      the proportion by weight of water and ethanol with respect to the total weight of the polar solvent a1) is preferably at least about 60% by weight, preferably at least about 80% by weight, particularly preferably at least about 90% by weight and in particular at least about 95% by weight and
      the proportion by weight of water to ethanol is about 5:1 to about 1:5, preferably about 2:1 to about 1:2 and in particular about 5:4 to about 4:5
   a2) about 0.5% to about 15% by weight of at least one copolymer selected from the monomers
      i) N-tert-octylacrylamide
      ii) acrylic acid iii) tert-butylaminoethylmethacrylate
iv) as well as other monomers if appropriate
b) a device for flash evaporation of the cosmetic preparation a), comprising
   b1) a container b1) which can be closed and opened by employing a valve
   b2) a heating device for heating a cosmetic preparation in the container b1)
   b3) a nozzle b3) for spraying the cosmetic preparation a).

A further essential component of the cosmetic compositions as contemplated herein is the copolymer a2). With regard to the manufacturing capability, applicability and cosmetic action of the cosmetic compositions as contemplated herein, it has been shown to be advantageous for the proportion by weight of the copolymer a2) with respect to the total weight of the cosmetic preparation a) to be about 1.0% to about 12% by weight, preferably about 3.0% to about 9.0% by weight.

The copolymer a2) can be based on the monomers i) N-tert-octylacrylamide, ii) acrylic acid, iii) tert-butylaminoethylmethacrylate as well as other appropriate monomers.

Preferred copolymers a2) are preferably at least about 90% by weight, preferably at least about 95% by weight and in particular at least about 97% by weight constituted by the monomers N-tert-octylacrylamide, acrylic acid and tert-butylaminoethylmethacrylate. Particularly preferred copolymers a2) were obtained exclusively from the monomers N-tert-octylacrylamide, acrylic acid and tert-butylaminoethylmethacrylate.

Copolymers a2) formed by the monomers i) N-tert-octylacrylamide, ii) acrylic acid, iii) tert-butylaminoethylmethacrylate, iv) methylmethacrylate and v) hydroxypropylmethacrylate are particularly preferred.

The copolymers a2) described above are sold, for example, under the trade names Amphomer® (INCI designation: octylacrylamide/acrylates/butylaminoethyl methacrylate copolymer; CAS number 70801-07-9) from National Starch.

A particularly preferred aspect of the present disclosure is therefore a cosmetic product comprising
a) a cosmetic preparation containing, with respect to its total weight
   a1) about 70% to about 98% by weight of at least one polar solvent;
   a2) about 3.0% to about 9.0% by weight of at least one copolymer selected from the monomers
      i) N-tert-octylacrylamide
      ii) acrylic acid
      iii) tert-butylaminoethylmethacrylate
      iv) methylmethacrylate
      v) hydroxypropylmethacrylate
b) a device for flash evaporation of the cosmetic preparation a).

In addition to the cosmetic preparation a), the cosmetic products as contemplated herein further comprise a device for flash evaporation. The expression "flash evaporation" as used in the context of the present disclosure means the generation of vapour when the pressure is dropped in a sealed chamber filled with liquid and under positive pressure (with respect to the environment). A positive pressure of this type can, for example, be produced by heating a quantity of the cosmetic preparation a) in a sealed chamber to a temperature T1. In the sealed chamber at the given temperature T1, the liquid has a saturated pressure p1. If the sealed chamber is opened, for example by employing a valve, to a relaxation chamber which is not under positive pressure but at a pressure p0<p1, then the pressure in the previously sealed chamber drops and in the process of decompressing to the new pressure, the cosmetic preparation a) vaporizes or the solvent contained in the cosmetic preparation or parts of this solvent vaporizes. The vapour or spray mist which is generated can be used for the application of specific cosmetic preparations.

Thus, if the cosmetic preparation a) is heated in a sealed chamber starting from standard conditions (T0=25° C., p0=1000 bar), then, in addition to an increased temperature, the pressure of the cosmetic preparation a) also increases. This raised pressure can then be relieved in a relaxation chamber to a pressure p0, for example to the pressure of the environment (p0=1000 bar), whereupon at least partial vaporization of the cosmetic preparation a) is obtained.

The cosmetic preparation a) may be directly depressurized in the chamber in which it had been heated. The heated and pressurized cosmetic preparation a) may alternatively, however, also be transported into a second chamber following heating, in which pressure release is subsequently carried out.

In other words, flash evaporation is a method in which the cosmetic preparation a) in a sealed container is heated using a heating device to temperatures above the environmental temperature, whereupon a pressure is generated in the container which is above the environmental pressure and the heated and pressurized cosmetic preparation a) is then released from the container into the environment.

A device for flash evaporation, therefore, is a device which comprises a container and a heating device and is configured in a manner such that a cosmetic preparation a) in the sealed container can be heated by employing the heating device to temperatures above the environmental temperature in a manner such that a pressure above the environmental pressure is generated in the container and the heated and pressurized cosmetic preparation a) can then be released from the container into the environment.

At the same time as or after releasing the pressure, the cosmetic preparation a) can be fed to a nozzle such that, for example, properties of the vapour or spray mist produced by the flash evaporation, in particular the droplet size or the droplet density, but also the spray range and the shape of the spray cone can be influenced. The use of nozzles, preferably spray nozzles, is therefore preferred. The specific nozzle type or the specific nozzle configuration will be determined in association with the respective spray mist properties.

In summary, a preferred device for flash evaporation is provided with
b1) a container b1) which can be closed and opened by employing a valve, which defines the sealed inner chamber in which the cosmetic preparation can be accommodated,
b2) a heating device b2), which allows a cosmetic preparation contained in the container b1) to be heated.

The use of an addition nozzle b3) which enables the cosmetic preparation a) released from the container to be sprayed is particularly preferred. As an alternative to a valve, a closure element which operates in a comparable manner, which can close or open an associated opening in the container by an appropriate change of position, may also be employed.

In a preferred aspect, the present disclosure provides a cosmetic product comprising
a) a cosmetic preparation containing, with respect to its total weight
   a1) about 45% to about 98% by weight of at least one polar solvent;

a2) about 0.5% to about 15% by weight of at least one copolymer selected from the monomers
  i) N-tert-octylacrylamide
  ii) acrylic acid
  iii) tert-butylaminoethylmethacrylate
  iv) as well as other monomers if appropriate;
b) a device for flash evaporation of the cosmetic preparation a), wherein the device for flash evaporation comprises a container b1) and a heating device b2) and is configured in a manner such that
  the cosmetic preparation a) can be accommodated in the inner chamber of the container b1),
  the inner chamber of the container b1) which is at least partially filled with the cosmetic preparation a) can be sealed,
  the cosmetic preparation a) in the sealed inner chamber of the container b1) can be heated by employing the heating device b2), with a concomitant rise in the pressure.

In a particularly preferred aspect of the present disclosure, therefore, a cosmetic product is provided comprising
a) a cosmetic preparation containing, with respect to its total weight
  a1) about 45% to about 98% by weight of at least one polar solvent;
  a2) about 0.5% to about 15% by weight of at least one copolymer selected from the monomers
    i) N-tert-octylacrylamide
    ii) acrylic acid
    iii) tert-butylaminoethylmethacrylate
    iv) as well as other monomers if appropriate
b) a device for flash evaporation of the cosmetic preparation a), comprising
  b1) a container b1) which can be closed and opened by employing a valve
  b2) a heating device for heating a cosmetic preparation in the container b1)
  b3) a nozzle b3) for spraying the cosmetic preparation a).

In other words, in a particularly preferred aspect of the present disclosure, a cosmetic product is provided comprising
a) a cosmetic preparation containing, with respect to its total weight
  a1) about 45% to about 98% by weight of at least one polar solvent;
  a2) about 0.5% to about 15% by weight of at least one copolymer selected from the monomers
    i) N-tert-octylacrylamide
    ii) acrylic acid
    iii) tert-butylaminoethylmethacrylate
    iv) as well as other monomers if appropriate;
b) a device for flash evaporation of the cosmetic preparation a), wherein the device for flash evaporation comprises a container b1) and a heating device b2) and is configured in a manner such that
  the cosmetic preparation a) can be accommodated in the inner chamber of the container b1),
  the inner chamber of the container b1) which is at least partially filled with the cosmetic preparation a) can be sealed,
  the cosmetic preparation a) in the sealed inner chamber of the container b1) can be heated by employing the heating device b2), with a concomitant rise in the pressure,
  the heated cosmetic preparation a) can be released into the environment from the inner chamber of the container b1) with a concomitant reduction in pressure.

The container b1) in which the cosmetic preparation is heated is configured in a manner which during heating of the cosmetic preparation a) allows this container to be completely sealed against the environment and after heating, allows it to open up for flash evaporation of the cosmetic preparation a). This may be achieved, for example, by using a component for controlling the flow, in particular a valve.

The container b1) in which the cosmetic preparation is heated is preferably in contact with a further container from which the required quantity of the cosmetic preparation is transferred into the container b1) prior to heating. In this regard, the access between this reservoir and the container b1) is opened and closed via an appropriate means, for example a valve. This further container is preferably configured in the form of a reservoir, which means that it preferably comprises a multiple, for example more than ten times, preferably more than fifty times the quantity of cosmetic preparation required for one vaporization procedure. In other words, the further container/reservoir preferably holds a multiple, for example more than ten times the volume, preferably more than twenty times and in particular more than fifty times the volume of the container b1).

In a further particularly preferred aspect of the present disclosure, a cosmetic product is provided, comprising
a) a cosmetic preparation containing, with respect to its total weight
  a1) about 45% to about 98% by weight of at least one polar solvent;
  a2) about 0.5% to about 15% by weight of at least one copolymer selected from the monomers
    i) N-tert-octylacrylamide
    ii) acrylic acid
    iii) tert-butylaminoethylmethacrylate
    iv) as well as other monomers if appropriate;
b) a device for flash evaporation of the cosmetic preparation a), comprising
  b1) a container b1) which can be closed and opened by employing a valve
  b2) a heating device, which allows a cosmetic preparation contained in the sealed container b1) to be heated
  b3) a nozzle b3) for spraying the cosmetic preparation a)
c) a reservoir for the cosmetic preparation a), from which the cosmetic preparation a) can reach the container b1), wherein
  the access between the reservoir and container b1) is provided with a component for regulating flow, such that the flow of the cosmetic preparation a) from the reservoir into the container b1) can be interrupted;
  the reservoir holds at least ten times the volume, preferably at least twenty times and in particular at least fifty times the volume of the container b1).

The reservoir is not a pressurized container and the cosmetic preparation in the reservoir is not under pressure; in other words, the pressure inside the reservoir is the environmental pressure (also known as air pressure or atmospheric pressure). Thus, cosmetic products of this type do not contain a propellant. The cosmetic product also does not have a pump device which is suitable for releasing or spraying the cosmetic preparation into the environment without the action of the flash evaporation device.

In a more particularly preferred aspect, the present disclosure provides a cosmetic product comprising
a) a cosmetic preparation containing, with respect to its total weight
  a1) about 45% to about 98% by weight of at least one polar solvent;

a2) about 0.5% to about 15% by weight of at least one copolymer selected from the monomers
   i) N-tert-octylacrylamide
   ii) acrylic acid
   iii) tert-butylaminoethylmethacrylate
   iv) as well as other monomers if appropriate;
b) a device for flash evaporation of the cosmetic preparation a), comprising
   b1) a container b1) which can be closed and opened by employing a valve
   b2) a heating device for heating a cosmetic preparation in the sealed container b1)
   b3) a nozzle b3) for spraying the cosmetic preparation a)
c) a reservoir for the cosmetic preparation a), from which the cosmetic preparation a) can reach the container b1), wherein
   the access between the reservoir and container b1) is provided with a component for regulating flow, such that the flow of the cosmetic preparation a) from the reservoir into the container b1) can be interrupted;
   the reservoir holds at least ten times the volume, preferably at least fifty times the volume of the container b1);
   the pressure inside the reservoir corresponds to the pressure of the environment.

In a more particularly preferred aspect, the present disclosure provides a cosmetic product comprising
a) a cosmetic preparation containing, with respect to its total weight
   a1) about 45% to about 98% by weight of at least one polar solvent;
   a2) about 0.5% to about 15% by weight of at least one copolymer selected from the monomers
      i) N-tert-octylacrylamide
      ii) acrylic acid
      iii) tert-butylaminoethylmethacrylate
      iv) as well as other monomers if appropriate;
b) a device for flash evaporation of the cosmetic preparation a), comprising
   b1) a container b1) which can be closed and opened by employing a valve
   b2) a heating device for heating a cosmetic preparation in the sealed container b1)
   b3) a nozzle b3) for spraying the cosmetic preparation a)
c) a reservoir for the cosmetic preparation a), from which the cosmetic preparation a) can reach the container b1), wherein
   the access between the reservoir and container b1) is provided with a component for regulating flow, such that the flow of the cosmetic preparation a) from the reservoir into the container b1) can be interrupted;
   the reservoir holds at least ten times the volume, preferably at least fifty times the volume of the container b1);
   the pressure inside the reservoir corresponds to the pressure of the environment and the cosmetic product does not include a propellant.

Furthermore, cosmetic products are preferred which comprise
a) a cosmetic preparation containing, with respect to its total weight
   a1) about 45% to about 98% by weight of at least one polar solvent;
   a2) about 0.5% to about 15% by weight of at least one copolymer selected from the monomers
      i) N-tert-octylacrylamide
      ii) acrylic acid
      iii) tert-butylaminoethylmethacrylate
      iv) as well as other monomers if appropriate;
b) a device for flash evaporation of the cosmetic preparation a), comprising
   b1) a container b1) which can be closed and opened by employing a valve
   b2) a heating device for heating a cosmetic preparation in the sealed container b1)
   b3) a nozzle b3) for spraying the cosmetic preparation a).
c) a reservoir for the cosmetic preparation a), from which the cosmetic preparation a) can reach the container b1), wherein
   the access between the reservoir and container b1) is provided with a component for regulating flow, such that the flow of the cosmetic preparation a) from the reservoir into the container b1) can be interrupted;
   the reservoir holds at least ten times the volume, preferably at least fifty times the volume of the container b1);
   the pressure inside the reservoir corresponds to the pressure of the environment, wherein the cosmetic product does not have a pump means which is suitable for releasing or spraying the cosmetic preparation a) without the action of the device for flash evaporation.

In summary, in a particularly preferred aspect, the present disclosure therefore provides a cosmetic product comprising
a) a cosmetic preparation containing, with respect to its total weight
   a1) about 45% to about 98% by weight of at least one polar solvent;
   a2) about 0.5% to about 15% by weight of at least one copolymer selected from the monomers
      i) N-tert-octylacrylamide
      ii) acrylic acid
      iii) tert-butylaminoethylmethacrylate
      iv) as well as other monomers if appropriate
b) a device for flash evaporation of the cosmetic preparation a), comprising
   b1) a container b1) which can be closed and opened by employing a valve
   b2) a heating device for heating a cosmetic preparation in the sealed container b1)
   b3) a nozzle b3) for spraying the cosmetic preparation a)
c) a reservoir for the cosmetic preparation a), from which the cosmetic preparation a) can reach the container b1), wherein
   the access between the reservoir and container b1) is provided with a component for regulating flow, such that the flow of the cosmetic preparation a) from the reservoir into the container b1) can be interrupted;
   the reservoir holds at least about ten times the volume, preferably at least about fifty times the volume of the container b1);
   the pressure inside the reservoir corresponds to the pressure of the environment and the cosmetic product does not include a propellant,
wherein the cosmetic product does not have a pump means which is suitable for releasing or spraying the cosmetic preparation a) without the action of the device for flash evaporation.

In addition to the two components a1) and a2) described above, the cosmetic preparations a) as contemplated herein may contain further substances or excipients, wherein in particular those substances or excipients are preferred which improve the manufacturing capability, applicability and/or cosmetic effect of the cosmetic preparations as contemplated herein.

A first group of preferred further substances is formed by poly-($C_2$-$C_3$)alkylene glycol-modified silicones a3). Poly- ($C_2$-$C_3$)alkylene glycol-modified silicones from the group formed by alkoxylated dimethicones are preferred, in particular:
- ethoxylated dimethicones with the INCI designation PEG-x dimethicones with x=2 to 20, preferably 3 to 17 and in particular 11 or 12;
- ethoxylated dimethicones with the INCI designation bis-PEG-y dimethicones with x=3 to 25, preferably 4 to 20;
- ethoxylated/propoxylated dimethicones with the INCI designation PEG/PPG a/b dimethicones, wherein a and b independently of each other represent numbers from 2 to 30, preferably 12 to 24 and in particular 14 to 20;
- ethoxylated/propoxylated dimethicones with the INCI designation bis-PEG/PPG-c/d dimethicones, wherein c and d independently of each other represent numbers from 10 to 25, preferably 14 to 20 and in particular 14 to 16;
- ethoxylated/propoxylated dimethicones with the INCI designation bis-PEG/PPG-e/f PEG/PPG g/h dimethicones, wherein e, f, g and h independently of each other represent numbers from 10 to 20, preferably 14 to 18 and in particular 16.

In a first preferred embodiment, the cosmetic preparation a) contains, with respect to its total weight, about 0.0001% to about 1.0% by weight, preferably about 0.0002% to about 0.8% by weight and in particular about 0.0005% to about 0.5% by weight of at least one poly-($C_2$-$C_3$)alkylene glycol-modified silicone a3).

Particularly preferably, poly-($C_2$-$C_3$)alkylene glycol-modified silicone a3) from the group formed by alkoxylated dimethicones is used, preferably from the group formed by ethoxylated dimethicones and in particular from the group formed by compounds with the INCI designation PEG-12 dimethicones.

Further examples of further substances and excipients are the film-forming polymers a4), which are particularly preferably used in the cosmetic agents as contemplated herein.

Suitable film-forming polymers a4) are permanent as well as temporary cationic, anionic, nonionic or amphoteric polymers. These film-forming polymers may be of synthetic or natural origin. Preferred cosmetic preparations a) contain, with respect to their total weight, about 0.1% to about 10% by weight, preferably about 0.2% to about 8.0% by weight, and in particular about 0.5% to about 5.0% by weight of a film-forming polymer a4). This polymer a4) differs from the polymer a2).

Examples of routinely used film-forming polymers a4) are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethyleneglycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicones/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhy drophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVPNA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculiaurens gum, terephthalic acid/isophthalic acid/sodium isophthalic acid sulfonate/glycol copolymer, trimethylolpropane triacrylate, trimethylsiloxy silyl-carbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinylbutyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylatee copolymer, VP/DMAPA acrylates copolymer, VP/hexadecene copolymer, VP/VA copolymer, VP/vinyl capro-lactam/ DMAPA acrylates copolymer, yeast palmitate and styrene/ VP copolymer.

Particularly preferred cosmetic products are characterized in that the film-forming polymer a4) is selected from the group formed by anionic polymers, preferably from the group formed by copolymers of acrylic acid and methacrylic acid.

A particularly preferred anionic acrylate copolymer a4) is formed from at least the following monomer units: at least one (meth)acrylic acid unit (1), at least one (meth)acrylic acid alkylester unit (2) and at least one (meth)acrylic acid hydroxyalkylester unit (3). As contemplated herein, this preferred copolymer a4) may be formed from further monomer units. In accordance with embodiments as contemplated herein, however, the copolymer a4) is solely formed from the units (1), (2) and (3), i.e. it consists of units derived from these monomer units.

The at least one methacrylic acid unit (1) may be a methacrylic acid or acrylic acid unit.

The alkyl residue of the (meth)acrylic acid alkylester unit (2) is preferably a C1-C8 alkyl residue, which may be linear or branched. Examples of alkyl residues are methyl, ethyl, propyl, isopropyl, 1-butyl, 2-butyl, iso-butyl, tert-butyl, linear or branched pentyl, linear or branched hexyl, linear or branched heptyl and linear or branched octyl. The alkyl group of a C1 to C5 alkyl group is preferred. In accordance with one embodiment as contemplated herein, two or more (meth)acrylic acid alkylester units (2) are present which differ from the alkyl group in the number of carbon atoms. Examples are a C1-C3 alkylmethacrylate unit and a C2-C5 alkylacrylate unit.

The hydroxyalkyl residue of the (meth)acrylic acid hydroxyalkylester unit (3) may be a hydroxy-C1-C10 alkyl residue, preferably a hydroxy-C2-C5 alkyl residue. In a preferred embodiment, the (meth)acrylic acid hydroxyalkylester unit (3) is (meth)acrylic acid hydroxyethylester.

The proportion of units (1), (2) and (3) in the acrylate resin a4) may vary widely. The proportion of the unit (1) in the acrylate copolymer is preferably about 2% to about 50% by weight, more preferably about 5% to about 30% by weight. The proportion of unit (2) in the acrylate copolymer is preferably about 5% to about 95% by weight, more preferably about 45% to about 90% by weight. The proportion of unit (3) in the acrylate copolymer is preferably about 2% to about 70% by weight, more preferably about 5% to about 30% by weight.

Suitable anionic acrylate copolymers a4) are commercially available under the INCI designation acrylates/hydroxyesters acrylates copolymer. The most preferably preferred anionic acrylate copolymer (a) is Acudyne® 1000 from The Dow Chemical Company.

A further preferred anionic acrylate copolymer a4) comprises structural units with formula (4) wherein R1 represents a methyl group and R2 represents a methyl group, and structural units with formula (4) wherein R1 represents a hydrogen atom and R2 represents a butyl group (in particular a n-butyl group), and structural units with formula (5) wherein R3 represents a methyl group and R4 represents a 2-hydroxyethyl group, and structural units with formula (6) wherein R7 represents a methyl group, at least one structural unit with formula (7) wherein R5 and $R^6$ independently of each other represent a hydrogen atom or a ($C_1$ to $C_6$) alkyl group, preferably hydrogen

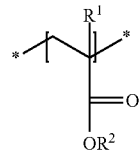

(4)

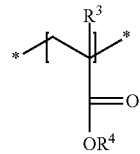

(5)

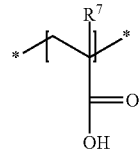

(6)

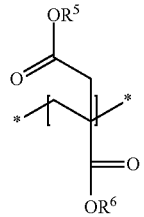

(7)

A particularly preferred polymer has the INCI nomenclature acrylates/C1-2 succinates/hydroxyacrylates copolymer. It may, for example, be obtained under the trade name Acudyne LT-120 from Dow (INCI nomenclature: acrylates/C1-2 succinates/hydroxyacrylates copolymer).

A second preferred group in the polymer a4) used in the cosmetic preparation is that of the vinylpyrrolidone homo- or copolymers B. Examples of particularly preferred polymers B are as follows:

polyvinylpyrrolidones, for example those marketed under the trade name Luviskol®(BASF), vinylpyrrolidone/vinylester-copolymers, for example those marketed under the trade name Luviskol® (BASF). Luviskol®VA 64 and Luviskol®VA 73, both vinylpyrrolidone/vinylacetate copolymers, are preferred nonionic polymers.

Because of their cosmetic action in combination with the copolymers a2) of the film-forming polymers used as contemplated herein, polyvinylpyrrolidones (INCI designation: PVP) as well as vinylpyrrolidone/vinylacetate copolymers (INCI designation VP/VA copolymer) are preferred. Preferred cosmetic products are wherein the film-forming polymer a4) is selected from the group of nonionic polymers, preferably from the group formed by polyvinylpyrrolidone and vinylpyrrolidone/vinylacetate copolymers, preferably polyvinylpyrrolidones.

A third particularly preferred group of film-forming polymers a4) comprises amphoteric solidifying polymers C based on:

at least one monomer C1 selected from acrylic acid, methacrylic acid, acrylic acid alkyl esters and methacrylic acid alkyl esters, and at least one amphoteric monomer C2 with formula C2

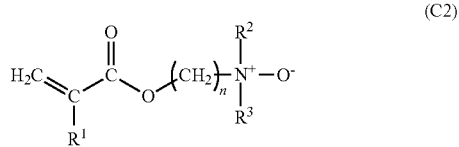

wherein
$R^1$ represents H or $CH_3$
$R^2$ and $R^3$, each independently of each other, represent optionally branched $C_1$-$C_{10}$ alkyl, and
n represents a whole number from 1 to 20.

The term "additional amphoteric firming polymers" formed by said monomers and in the context of the present embodiment as contemplated herein means only those copolymers C which, in addition to polymer units which result from incorporating said monomers C1 and C2 into the copolymer, contain a maximum of about 5% by weight, advantageously a maximum of about 1% by weight of polymer units which are based on the incorporation of other monomers. Preferably, the copolymers C are exclusively constructed from polymer units which result from the incorporation of said monomers C1 and C2 into the copolymer.

Suitable monomers C1 are acrylic acid, methacrylic acid, acrylic acid C1-C20-alkylesters and methacrylic acid C1-C20-alkylesters. Particularly preferably, monomer C1 is selected from acrylic acid, methacrylic acid, acrylic acid methylester, methacrylic acid methylester, acrylic acid ethylester, methacrylic acid ethylester, acrylic acid propylester, methacrylic acid propylester, acrylic acid isopropylester, methacrylic acid isopropylester, acrylic acid laurylester, methacrylic acid laurylester, acrylic acid cetylester, methacrylic acid cetylester, acrylic acid stearylester and methacrylic acid stearylester, more particularly preferably from acrylic acid, methacrylic acid, acrylic acid methylester, methacrylic acid methylester, acrylic acid ethylester, methacrylic acid ethylester, acrylic acid laurylester, methacrylic acid laurylester, acrylic acid stearylester and methacrylic acid stearylester.

Suitable monomers C2 are (meth)acryloylalkylaminoxides with formula C2, wherein R2 and R3 each independently of each other represent methyl, ethyl, propyl, isopropyl, butyl, isobutyl or tert-butyl, particularly preferably methyl. Suitable monomers C2 are furthermore selected from at least one monomer from the group formed by (meth)acryloylalkylaminoxides with formula C2, wherein n represents a whole number from 1 to 5, preferably a whole number from 1 to 3 and particularly preferably represents 2.

Monomers C2 selected from at least one monomer selected from the group formed by (meth)acryloylalkylaminoxides with formula C2, wherein R1 represents CH3, are also preferred.

Monomers C2 selected from at least one monomer from the group formed by (meth)acryloylalkylaminoxides with formula C2 are particularly suitable, wherein $R^2$ and $R^3$ independently of each other represent methyl, ethyl, propyl, isopropyl, butyl, isobutyl or tert-butyl, particularly preferably methyl, n respectively represents a whole number from 1 to 5, preferably a whole number from 1 to 3 and particularly preferably represents 2, and $R^1$ respectively represents $CH_3$. The monomer C2 selected from at least one monomer from the group formed by (meth)acryloylalkylaminoxides with formula C2, wherein $R^1$, $R^2$ and $R^3$ represent $CH_3$ and n represents 2, are especially suitable. Preferred cosmetic products are wherein the film-forming polymer a4) is selected from the group formed by copolymers of methacryloylethyl-N,N-dimethylaminoxide.

In a particularly suitable embodiment, the cosmetic preparation as contemplated herein contains at least one amphoteric firming polymer which is formed by
at least two monomers C1, wherein the first monomer is selected from acrylic acid, methacrylic acid, acrylic acid methylester, methacrylic acid methylester, acrylic acid ethylester, methacrylic acid ethylester, acrylic acid propylester, methacrylic acid propylester, acrylic acid isopropylester and methacrylic acid isopropylester, and the second monomer is selected from acrylic acid stearylester and methacrylic acid stearylester, and
methacryloylethylaminoxide as the monomer C2, in particular methacryloylethyl-N,N-dimethylaminoxide (in formula (A2): $R^1$=$CH_3$, n=2, $R^2$ and $R^3$=$CH_3$).

These copolymers are also known and may, for example, be obtained from Clariant under the designation Diaformer Z-632, wherein the use of Diaformer Z-632 is particularly preferred.

In a suitable embodiment, the agent as contemplated herein contains at least one amphoteric firming polymer which is selected from
at least three monomers C1, wherein the first monomer is selected from acrylic acid, methacrylic acid, acrylic acidmethylester, methacrylic acid methylester, acrylic acid ethylester, methacrylic acid ethylester, acrylic acid propylester, methacrylic acid propylester, acrylic acid isopropylester and methacrylic acid isopropylester, the second monomer is selected from acrylic acid laurylester and methacrylic acid laurylester, and the third monomer is selected from acrylic acid stearylester and methacrylic acid stearylester, and
methacryloylethylaminoxide as the monomer C2, in particular methacryloylethyl-N,N-dimethylaminoxide (in formula (A2): $R^1$=$CH_3$, n=2, $R^2$ and $R^3$=$CH_3$).

The corresponding copolymers are also known and obtainable, for example, under the designations Diaformer Z-611, Diaformer Z-612, Diaformer Z-613, Diaformer Z-631, Diaformer Z-633, Diaformer Z-651, Diaformer Z-711 N, Diaformer Z-712N and Diaformer Z-731 N from Clariant, wherein the use of Diaformer Z-712N and Diaformer Z-651 is preferred.

To improve the manufacturing capability, applicability and cosmetic action, the cosmetic preparation a) preferably contains nonionic surfactants a5), wherein particularly preferred cosmetic preparations a) wherein they contain about 0.05% to about 4.0% by weight, preferably about 0.1% to about 2.0% by weight and in particular about 0.2% to about 1.0% by weight of nonionic surfactant a5).

Preferred nonionic surfactants are PEG derivatives of hydrogenated castor oil which, for example, can be obtained under the designation of PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil or PEG-60 Hydrogenated Castor Oil. Particularly preferred nonionic surfactants as contemplated herein are selected from the group formed by PEG derivatives of hydrogenated castor oil, particularly preferably from the group PEG-40 Hydrogenated Castor Oil and PEG-60 Hydrogenated Castor Oil.

A further group of preferred substances is formed by ester oils a6). The term "ester oils" as used herein should be understood to mean esters of C6-C30 fatty acids with C2-C30 fatty alcohols. Monoesters of the fatty acids with alcohols containing 2 to 24 C atoms are preferred. Particularly preferred compounds as contemplated herein are isopropylmyristate (Rilanit®IPM), isononanoic acid-C16-18-alkylester (Cetiol®SN), 2-ethylhexylpalmitate (Cegesoft®24), stearic acid 2-ethylhexylester (Cetiol®868), cetyl oleate, glycerine tricaprylate, coconut oil alcohol-caprinate/-caprylate (Cetiol®LC), n-butylstearate, oleyl erucate (Cetiol®J 600), isopropylpalmitate (Rilanit®IPP), oleyl oleate (Cetiol®), lauric acid hexylester (Cetiol®A), di-n-butyladipate (Cetiol®B), myristyl myristate (Cetiol®MM), cetearyl isononanoate (Cetiol®SN), oleic acid decylester (Cetiol®V). In preferred cosmetic preparations a) as contemplated herein, the proportion by weight of the ester oil a6) with respect to the total weight of the cosmetic preparation a) is about 0.01% to about 1.5% by weight, preferably about 0.05% to about 1.0% by weight and in particular about 0.1% to about 0.8% by weight. Particularly preferably, the ester oil a6) is a compound from the group formed by monoesters of $C_6$-$C_{30}$ fatty acids with $C_2$-$C_{24}$ fatty alcohols, in particular isopropylmyristate.

Additional care products may also be cited in respect of further suitable substances or excipients.

The agent may, for example, contain at least one protein hydrolysate and/or one of its derivatives as a care product. Protein hydrolysates are mixtures of substances which are obtained by the acidic, basic or enzymatically catalysed degradation of proteins. The term "protein hydrolysates" as used in the invention should be understood to mean total hydrolysates as well as individual amino acids and their derivatives, as well as mixtures of various amino acids. The molecular weight of the protein hydrolysates used as contemplated herein is between about 75, the molecular weight of glycine, and about 200000; preferably, the molecular weight is about 75 to about 50000 and more particularly preferably about 75 to about 20000 Dalton.

The agent as contemplated herein may also contain at least one vitamin, a provitamin, a vitamin precursor and/or one of its derivatives as the care product. In this regard, preferred vitamins, provitamins and vitamin precursors are those assigned to the groups A, B, C, E, F and H.

Further care products are panthenol, caffeine, nicotinamide and sorbitol.

The agent as contemplated herein may also contain at least one plant extract as the care product, as well as mono- or oligosaccharides and/or lipids.

The composition of some particularly preferred cosmetic preparations as contemplated herein can be obtained from the following tables (percentages given as the % by weight with respect to the total weight of the cosmetic agent unless stated otherwise). Regarding further preferred embodiments of these particularly preferred compositions, the statements provided above regarding the cosmetic preparations a) as contemplated herein apply mutatis mutandis.

|  | Formula 1 | Formula 2 | Formula 3 | Formula 4 | Formula 5 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Optional additives | add 100 | add 100 | add 100 | add 100 | add 100 |

|  | Formula 6 | Formula 7 | Formula 8 | Formula 9 | Formula 10 |
|---|---|---|---|---|---|
| Polar solvent a1) | 45 to 98 | 55 to 92 | 70 to 90 | 81 | 93 |
| Copolymer a2)[1] | 0.5 to 15 | 1.0 to 12 | 3.0 to 9.0 | 8.5 | 0.6 |
| Optional additives | add 100 | add 100 | add 100 | add 100 | add 100 |

|  | Formula 11 | Formula 12 | Formula 13 | Formula 14 | Formula 15 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Poly-($C_2$-$C_3$)alkyleneglycol-modified silicone a3) | 0.0001 to 1.0 | 0.0002 to 0.8 | 0.0005 to 0.5 | 0.002 | 0.00015 |
| Optional additives | add 100 | add 100 | add 100 | add 100 | add 100 |

|  | Formula 16 | Formula 17 | Formula 18 | Formula 19 | Formula 20 |
|---|---|---|---|---|---|
| Polar solvent a1) | 45 to 98 | 55 to 92 | 70 to 90 | 81 | 93 |
| Copolymer a2)[1] | 0.5 to 15 | 1.0 to 12 | 3.0 to 9.0 | 8.5 | 0.6 |
| PEG-12 dimethicone | 0.0001 to 1.0 | 0.0002 to 0.8 | 0.0005 to 0.5 | 0.002 | 0.00015 |
| Optional additives | add 100 | add 100 | add 100 | add 100 | add 100 |

|  | Formula 21 | Formula 22 | Formula 23 | Formula 24 | Formula 25 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Polymer a4) | 0.1 to 10 | 0.2 to 8.0 | 0.5 to 5.0 | 0.9 | 0.9 |
| Optional additives | add 100 | add 100 | add 100 | add 100 | add 100 |

|  | Formula 26 | Formula 27 | Formula 28 | Formula 29 | Formula 30 |
|---|---|---|---|---|---|
| Polar solvent a1) | 45 to 98 | 55 to 92 | 70 to 90 | 81 | 93 |
| Copolymer a2)[1] | 0.5 to 15 | 1.0 to 12 | 3.0 to 9.0 | 8.5 | 0.6 |
| (Meth)acrylic acid copolymer | 0.1 to 10 | 0.2 to 8.0 | 0.5 to 5.0 | 0.9 | 0.9 |
| Optional additives | add 100 | add 100 | add 100 | add 100 | add 100 |

-continued

|  | Formula 31 | Formula 32 | Formula 33 | Formula 34 | Formula 35 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 1.5 | 0.6 |
| Vinylpyrrolidone/vinyl acetate copolymer | 0.1 to 10 | 0.2 to 8.0 | 0.5 to 5.0 | 4.3 | 2.2 |
| Optional additives | add 100 | add 100 | add 100 | add 100 | add 100 |

|  | Formula 36 | Formula 37 | Formula 38 | Formula 39 | Formula 40 |
|---|---|---|---|---|---|
| Polar solvent a1) | 45 to 98 | 55 to 92 | 70 to 90 | 81 | 93 |
| Copolymer a2)[1)] | 0.5 to 15 | 1.0 to 12 | 3.0 to 9.0 | 2.4 | 1.2 |
| Methacryloylethyl-N,N-dimethylaminooxide copolymer | 0.1 to 10 | 0.2 to 8.0 | 0.5 to 5.0 | 1.8 | 1.8 |
| Optional additives | add 100 | add 100 | add 100 | add 100 | add 100 |

|  | Formula 41 | Formula 42 | Formula 43 | Formula 44 | Formula 45 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Nonionic surfactant a5) | 0.05 to 4.0 | 0.1 to 2.0 | 0.2 to 1.0 | 0.2 | 0.5 |
| Optional additives | add 100 | add 100 | add 100 | add 100 | add 100 |

|  | Formula 46 | Formula 47 | Formula 48 | Formula 49 | Formula 50 |
|---|---|---|---|---|---|
| Polar solvent a1) | 45 to 98 | 55 to 92 | 70 to 90 | 81 | 93 |
| Copolymer a2)[1)] | 0.5 to 15 | 1.0 to 12 | 3.0 to 9.0 | 8.5 | 0.6 |
| PEG-40 Hydrogenated Castor Oil | 0.05 to 4.0 | 0.1 to 2.0 | 0.2 to 1.0 | 0.2 | 0.5 |
| Optional additives | add 100 | add 100 | add 100 | add 100 | add 100 |

|  | Formula 51 | Formula 52 | Formula 53 | Formula 54 | Formula 55 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Ester oil a6) | 0.01 to 1.5 | 0.05 to 1.0 | 0.1 to 0.8 | 0.1 | 0.2 |
| Optional additives | add 100 | add 100 | add 100 | add 100 | add 100 |

|  | Formula 56 | Formula 57 | Formula 58 | Formula 59 | Formula 60 |
|---|---|---|---|---|---|
| Polar solvent a1) | 45 to 98 | 55 to 92 | 70 to 90 | 81 | 93 |
| Copolymer a2)[1)] | 0.5 to 15 | 1.0 to 12 | 3.0 to 9.0 | 8.5 | 0.6 |
| Isopropylmyristate | 0.01 to 1.5 | 0.05 to 1.0 | 0.1 to 0.8 | 0.1 | 0.2 |
| Optional additives | add 100 | add 100 | add 100 | add 100 | add 100 |

|  | Formula 61 | Formula 62 | Formula 63 | Formula 64 | Formula 65 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Poly-($C_2$-$C_3$)alkyleneglycol-modified silicone a3) | 0.0001 to 1.0 | 0.0002 to 0.8 | 0.0005 to 0.5 | 0.002 | 0.00015 |
| Polymer a4) | 0.1 to 10 | 0.2 to 8.0 | 0.5 to 5.0 | 0.9 | 0.9 |
| Optional additives | add 100 | add 100 | add 100 | add 100 | add 100 |

|  | Formula 66 | Formula 67 | Formula 68 | Formula 69 | Formula 70 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| PEG-12 dimethicone | 0.0001 to 1.0 | 0.0002 to 0.8 | 0.0005 to 0.5 | 0.002 | 0.00015 |
| Polymer a4) | 0.1 to 10 | 0.2 to 8.0 | 0.5 to 5.0 | 0.9 | 0.9 |
| Optional additives | add 100 | add 100 | add 100 | add 100 | add 100 |

|  | Formula 71 | Formula 72 | Formula 73 | Formula 74 | Formula 75 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Poly-($C_2$-$C_3$)alkyleneglycol- | 0.0001 to | 0.0002 to | 0.0005 to | 0.002 | 0.00015 |

-continued

| | | | | | |
|---|---|---|---|---|---|
| modified silicone a3) | 1.0 | 0.8 | 0.5 | | |
| (Meth)acrylic acid copolymer | 0.1 to 10 | 0.2 to 8.0 | 0.5 to 5.0 | 0.9 | 0.9 |
| Optional additives | add 100 | add 100 | add 100 | add 100 | add 100 |

| | Formula 76 | Formula 77 | Formula 78 | Formula 79 | Formula 80 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Poly-($C_2$-$C_3$)alkyleneglycol-modified silicone a3) | 0.0001 to 1.0 | 0.0002 to 0.8 | 0.0005 to 0.5 | 0.002 | 0.00015 |
| Vinylpyrrolidone/vinyl acetate copolymer | 0.1 to 10 | 0.2 to 8.0 | 0.5 to 5.0 | 0.9 | 0.9 |
| Optional additives | add 100 | add 100 | add 100 | add 100 | add 100 |

| | Formula 81 | Formula 82 | Formula 83 | Formula 84 | Formula 85 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Polymer a4) | 0.1 to 10 | 0.2 to 8.0 | 0.5 to 5.0 | 0.9 | 0.9 |
| Nonionic surfactant a5) | 0.05 to 4.0 | 0.1 to 2.0 | 0.2 to 1.0 | 0.2 | 0.5 |
| Optional additives | add 100 | add 100 | add 100 | add 100 | add 100 |

| | Formula 86 | Formula 87 | Formula 88 | Formula 89 | Formula 90 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Polymer a4) | 0.1 to 10 | 0.2 to 8.0 | 0.5 to 5.0 | 0.9 | 0.9 |
| PEG-40 Hydrogenated Castor Oil | 0.05 to 4.0 | 0.1 to 2.0 | 0.2 to 1.0 | 0.2 | 0.5 |
| Optional additives | add 100 | add 100 | add 100 | add 100 | add 100 |

| | Formula 91 | Formula 92 | Formula 93 | Formula 94 | Formula 95 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| (Meth)acrylic acid copolymer | 0.1 to 10 | 0.2 to 8.0 | 0.5 to 5.0 | 0.9 | 0.9 |
| Nonionic surfactant a5) | 0.05 to 4.0 | 0.1 to 2.0 | 0.2 to 1.0 | 0.2 | 0.5 |
| Optional additives | add 100 | add 100 | add 100 | add 100 | add 100 |

| | Formula 96 | Formula 97 | Formula 98 | Formula 99 | Formula 100 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Vinylpyrrolidone/vinyl acetate copolymer | 0.1 to 10 | 0.2 to 8.0 | 0.5 to 5.0 | 0.9 | 0.9 |
| Nonionic surfactant a5) | 0.05 to 4.0 | 0.1 to 2.0 | 0.2 to 1.0 | 0.2 | 0.5 |
| Optional additives | add 100 | add 100 | add 100 | add 100 | add 100 |

| | Formula 101 | Formula 102 | Formula 103 | Formula 104 | Formula 105 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Polymer a4) | 0.1 to 10 | 0.2 to 8.0 | 0.5 to 5.0 | 0.9 | 0.9 |
| Ester oil a6) | 0.01 to 1.5 | 0.05 to 1.0 | 0.1 to 0.8 | 0.1 | 0.2 |
| Optional additives | add 100 | add 100 | add 100 | add 100 | add 100 |

| | Formula 106 | Formula 107 | Formula 108 | Formula 109 | Formula 110 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Polymer a4) | 0.1 to 10 | 0.2 to 8.0 | 0.5 to 5.0 | 0.9 | 0.9 |
| Isopropylmyristate | 0.01 to 1.5 | 0.05 to 1.0 | 0.1 to 0.8 | 0.1 | 0.2 |
| Optional additives | add 100 | add 100 | add 100 | add 100 | add 100 |

-continued

|  | Formula 111 | Formula 112 | Formula 113 | Formula 114 | Formula 115 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| (Meth)acrylic acid copolymer | 0.1 to 10 | 0.2 to 8.0 | 0.5 to 5.0 | 0.9 | 0.9 |
| Ester oil a6) | 0.01 to 1.5 | 0.05 to 1.0 | 0.1 to 0.8 | 0.1 | 0.2 |
| Optional additives | add 100 | add 100 | add 100 | add 100 | add 100 |

|  | Formula 116 | Formula 117 | Formula 118 | Formula 119 | Formula 120 |
|---|---|---|---|---|---|
| Polar solvent a1) | 45 to 98 | 55 to 92 | 70 to 90 | 81 | 93 |
| Copolymer a2) | 0.5 to 15 | 1.0 to 12 | 3.0 to 9.0 | 8.5 | 0.6 |
| Vinylpyrrolidone/vinyl acetate copolymer | 0.1 to 10 | 0.2 to 8.0 | 0.5 to 5.0 | 0.9 | 0.9 |
| Ester oil a6) | 0.01 to 1.5 | 0.05 to 1.0 | 0.1 to 0.8 | 0.1 | 0.2 |
| Optional additives | add 100 | add 100 | add 100 | add 100 | add 100 |

[1])copolymer with the INCI designation octylacrylamide/acrylates/butylaminoethyl methacrylate copolymer In addition to the components a1) to a6) described above, more particularly preferred cosmetic preparations contain only small quantities of further substances and excipients. Cosmetic preparations which wherein the proportion by weight of components a1), a2) as well as, if present, a3) and/or a4) and/or a5) and/or a6) with respect to the total weight of the cosmetic preparation in an amount of at least about 80% by weight, preferably at least about 90% by weight, particularly preferably at least about 93% by weight and in particular at least about 97% by weight, because of their ready manufacturing capability and good cosmetic action, are particularly preferred. More particularly preferred cosmetic preparations consist, with respect to their total weight, of at least about 80% by weight, preferably at least about 87% by weight and in particular at least about 95% by weight of components a1) and a2).

As mentioned above, the cosmetic preparations a) as contemplated herein are particularly suitable for application by employing a device for flash evaporation. Thus, in a further aspect, the present application concerns the use of a cosmetic preparation a) containing, with respect to its total weight, a1) about 45% to about 98% by weight of at least one polar solvent;
a2) about 0.5% to about 15% by weight of at least one copolymer selected from the monomers
  i) N-tert-octylacrylamide
  ii) acrylic acid
  iii) tert-butylaminoethylmethacrylate
  iv) as well as other monomers if appropriate
as the process material in a device for flash evaporation.

In addition, the present application concerns the use of a product as contemplated herein for application to keratinic fibers, in particular human hair, with a cosmetic a) or for temporary shaping of keratinic fibers, in particular human hair.

In a further aspect of the present disclosure, a method is provided for the temporary shaping of preparation keratinic fibers, in particular human hair, in which a device for flash evaporation is used to apply a cosmetic preparation a) containing, with respect to its total weight a1) about 45% to about 98% by weight of at least one polar solvent;
a2) about 0.5% to about 15% by weight of at least one copolymer selected from the monomers
  i) N-tert-octylacrylamide
  ii) acrylic acid
  iii) tert-butylaminoethylmethacrylate
  iv) as well as other monomers if appropriate
to the keratinic fibers. The cosmetic preparation a) is preferably transformed by the device for flash evaporation into a spray mist which is then applied to the keratinic fibers.

In order to obtain a sufficient spray effect, the cosmetic preparation a) is preferably heated to temperatures above the boiling point of the polar solvent or solvent mixture contained in the cosmetic preparation a).

If the polar solvent is water or solvent mixtures with a water content of more than about 50% by weight (with respect to the total weight of the solvent mixture), the cosmetic preparation is preferably heated to temperatures over about 100° C., preferably to temperatures of about 100° C. and about 240° C., particularly preferably to temperatures of about 140° C. to about 160° C.

In cases in which the polar solvent is water or solvent mixtures with a proportion of water of more than about 50% by weight (with respect to the total weight of the solvent mixture), the positive pressure obtained by the heating is advantageously between about 1.1 and about 8 bar, preferably between about 1.2 and about 4 bar.

A preferred aspect of the application is a method for changing the colour of keratinic fibers, in particular human hair, in which a device for flash evaporation is used to apply a cosmetic preparation a) containing, with respect to its total weight:

a1) about 45% to about 98% by weight of at least one polar solvent;
a2) about 0.5% to about 15% by weight of at least one copolymer selected from the monomers
  i) N-tert-octylacrylamide
  ii) acrylic acid
  iii) tert-butylaminoethylmethacrylate
  iv) as well as other monomers if appropriate
to the keratinic fibers,
wherein
  a part quantity of the cosmetic preparation a) contained in a reservoir inside which a pressure prevails which corresponds to the environmental pressure is transferred into a container b1);
  next, the access between the reservoir and container b1) is interrupted by employing a component for controlling the flow such that the flow of the cosmetic preparation a) out of the reservoir into the container b1) can be interrupted;

next, the cosmetic preparation a) sealed against the environment in the container b1) is heated by employing a heating device so that the pressure inside the container b1) is raised to values above the environmental pressure, preferably to values between about 1.1 and about 8 bar, in particular to values between about 1.2 and about 4 bar;

next, the container b1) which is under a pressure which is above the environmental pressure is opened in a manner which decompresses and dispenses at least a part quantity, preferably at least about 50% by weight, preferably at least about 80% by weight and in particular at least about 90% by weight of the cosmetic preparation in the container b1) out of the container b1) into the environment with a concomitant reduction in the pressure in the container b1) prevailing at the moment of opening the container.

The release of the cosmetic preparation a) into the environment is preferably carried out along with the formation of a spray mist of the cosmetic preparation a).

The cosmetic preparation a) released from the container b1) is preferably applied to keratinic fibers, in particular human hair.

Methods wherein the cosmetic preparation released from the container b1) are fed through a nozzle prior to application to the keratinic fibers are particularly preferred.

Further preferred embodiments of the uses and of the method as contemplated herein follow mutatis mutandis from the cosmetic preparations a) as contemplated herein and the flash evaporation device b).

The agent, uses and methods as contemplated herein and some of their preferred embodiments are summarized and characterized through the following points:

1. A cosmetic product comprising
   a) a cosmetic preparation containing, with respect to its total weight
      a1) about 45% to about 98% by weight of at least one polar solvent;
      a2) about 0.5% to about 15% by weight of at least one copolymer selected from the monomers
         i) N-tert-octylacrylamide
         ii) acrylic acid
         iii) tert-butylaminoethylmethacrylate
         iv) as well as other monomers if appropriate
   b) a device for flash evaporation of the cosmetic preparation a).

2. The cosmetic product in accordance with point 1, wherein the device for flash evaporation comprises a container b1) and a heating device b2) and is configured in a manner such that
   the cosmetic preparation a) can be accommodated in the inner chamber of the container b1),
   the inner chamber of the container b1) which is at least partially filled with the cosmetic preparation a) can be sealed,
   the cosmetic preparation a) in the sealed inner chamber of the container b1) can be heated by employing the heating device b2), with a concomitant rise in the pressure,
   the heated cosmetic preparation a) can be released into the environment from the inner chamber of the container b1) with a concomitant reduction in pressure.

3. The cosmetic product in accordance with one of the preceding points, wherein the proportion by weight of the polar solvent a1) with respect to the total weight of the cosmetic preparation a) is about 55% to about 92% by weight, preferably about 70% to about 90% by weight.

4. The cosmetic product in accordance with one of the preceding points, wherein the polar solvent a1) has a boiling point (20° C., 1013 mbar) between about 50° C. and about 110° C., preferably between about 70° C. and about 105° C.

5. The cosmetic product in accordance with one of the preceding points, wherein the polar solvent a1) is selected from the group formed by ethanol, isopropanol and water.

6. The cosmetic product in accordance with one of the preceding points, wherein the proportion by weight of water and ethanol with respect to the total weight of the polar solvent a1) is at least about 60% by weight, preferably at least about 80% by weight, particularly preferably at least about 90% by weight and in particular at least about 95% by weight.

7. The cosmetic product in accordance with one of the preceding points, wherein the proportion by weight of water with respect to the total weight of the polar solvent a1) is more than about 80% by weight, preferably more than about 88% by weight and in particular more than about 92% by weight.

8. The cosmetic product in accordance with one of the preceding points, wherein the proportion by weight of ethanol with respect to the total weight of the cosmetic preparation is a maximum of about 55% by weight, preferably about 10% to about 55% by weight, particularly preferably about 25% to about 55% by weight and in particular about 40% to about 55% by weight.

9. The cosmetic product in accordance with one of the preceding points, wherein the polar solvent a1) comprises water and ethanol and the ratio by weight of water to ethanol is about 5:1 to about 1:5, preferably about 2:1 to about 1:2 and in particular 5:4 to 4:5.

10. The cosmetic product in accordance with one of the preceding points, wherein the proportion by weight of the copolymer a2) with respect to the total weight of the cosmetic preparation a) is about 1.0% to about 12% by weight, preferably about 3.0% to about 9.0% by weight.

11. The cosmetic product in accordance with one of the preceding points, wherein the cosmetic preparation a) contains, with respect to its total weight, about 0.0001% to about 1.0% by weight, preferably about 0.0002% to about 0.8% by weight and in particular about 0.0005% to about 0.5% by weight of at least one poly-$(C_2$-$C_3)$alkylene glycol-modified silicone a3).

12. The cosmetic product in accordance with point 11, wherein the poly-$(C_2$-$C_3)$alkylene glycol-modified silicone a3) is selected from the group formed by alkoxylated dimethicones, preferably from the group formed by ethoxylated dimethicones and in particular from the group formed by compounds with the INCI designation PEG-12 dimethicone.

13. The cosmetic product in accordance with one of the preceding points, wherein the cosmetic preparation a) contains, with respect to its total weight, about 0.1% to about 10% by weight, preferably about 0.2% to about 8.0% by weight, and in particular about 0.5% to about 5.0% by weight of a film-forming polymer a4).

14. The cosmetic product in accordance with point 13, wherein the film-forming polymer a4) is selected from the group formed by anionic polymers, preferably from the group formed by copolymers of acrylic acid and methacrylic acid.

15. The cosmetic product in accordance with point 13, wherein the film-forming polymer a4) is selected from the group formed by nonionic polymers, preferably from the group formed by polyvinylpyrrolidones and vinylpyrrolidone/vinylacetate copolymers, preferably polyvinylpyrrolidones.
16. The cosmetic product in accordance with point 13, wherein the film-forming polymer a4) is selected from the group formed by copolymers of methacryloylethyl-N,N-dimethylaminoxide.
17. The cosmetic product in accordance with one of the preceding points, wherein the cosmetic preparation a) contains, with respect to its total weight, about 0.05% to about 4.0% by weight, preferably about 0.1% to about 2.0% by weight and in particular about 0.2% to about 1.0% by weight of a nonionic surfactant a5).
18. The cosmetic product in accordance with point 17, wherein the nonionic surfactant is selected from the group formed by PEG derivatives of hydrogenated castor oil, particularly preferably from the group formed by PEG-40 Hydrogenated Castor Oil and PEG-40 Hydrogenated Castor Oil.
19. The cosmetic product in accordance with one of the preceding points, wherein the cosmetic preparation a) contains, with respect to its total weight, about 0.01% to about 1.5% by weight, preferably about 0.05% to about 1.0% by weight and in particular about 0.1% to about 0.8% % by weight of ester oil a6).
20. The cosmetic product in accordance with point 19, wherein the ester oil a6) is a compound from the group formed by monoesters of $C_6$-$C_{30}$ fatty acids with $C_2$-$C_{24}$ fatty alcohols, in particular isopropylmyristate.
21. Use of a cosmetic preparation a) containing, with respect to its total weight,
    a1) about 45% to about 98% by weight of at least one polar solvent;
    a2) about 0.5% to about 15% by weight of at least one copolymer selected from the monomers
        i) N-tert-octylacrylamide
        ii) acrylic acid
        iii) tert-butylaminoethylmethacrylate
        iv) as well as other monomers if appropriate
    as the process material in a device for flash evaporation.
22. Use of a product in accordance with one of points 1 to 20, for application of a cosmetic preparation a) to keratinic fibers, in particular human hair.
23. Use of a product in accordance with one of points 1 to 20, for the temporary shaping of keratinic fibers, in particular human hair.
24. A method for temporarily shaping keratinic fibers, in particular human hair, in which a cosmetic preparation a) is applied to the keratinic fibers using a device for flash evaporation containing, with respect to its total weight
    a1) about 45% to about 98% by weight of at least one polar solvent;
    a2) about 0.5% to about 15% by weight of at least one copolymer selected from the monomers
        i) N-tert-octylacrylamide
        ii) acrylic acid
        iii) tert-butylaminoethylmethacrylate
        iv) as well as other monomers if appropriate.
25. The method in accordance with point 24, wherein
    a part quantity of the cosmetic preparation a) contained in a reservoir inside which a pressure prevails which corresponds to the environmental pressure is transferred into a container b1);
    next, the access between the reservoir and container b1) is interrupted by employing a component for controlling the flow such that the flow of the cosmetic preparation a) out of the reservoir into the container b1) can be interrupted;
    next, the cosmetic preparation a) sealed against the environment in the container b1) is heated by employing a heating device so that the pressure inside the container b1) is raised to values above the environmental pressure, preferably to values between about 1.1 and about 8 bar, in particular to values between about 1.2 and about 4 bar;
    next, the container b1) which is under a pressure which is above the environmental pressure is opened in a manner which decompresses and dispenses at least a part quantity, preferably at least about 50% by weight, preferably at least about 80% by weight and in particular at least about 90% by weight of the cosmetic preparation in the container b1) out of the container b1) into the environment with a concomitant reduction in the pressure in the container b1) prevailing at the moment of opening the container.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic product comprising:
    a) a cosmetic preparation comprising, with respect to its total weight;
        a1) about 45% to about 98% by weight of at least one polar solvent; and
        a2) about 0.5% to about 15% by weight of at least one copolymer comprising the monomers:
            i) N-tert-octylacrylamide,
            ii) acrylic acid, and
            iii) tert-butylaminoethylmethacrylate; and
    b) a device for flash evaporation of the cosmetic preparation a), wherein the device for flash evaporation comprises:
    b1) a delivery container defining an interior in which the cosmetic preparation can be received;
    b2) a valve configured to selectively close and open the interior of the delivery container;
    b3) a heating apparatus for heating, under increased pressure, the cosmetic preparation in the interior of the delivery container when closed, and for releasing, under reduced pressure, the cosmetic preparation after heating from the interior of the delivery container into a surrounding environment;
    b4) a nozzle configured to atomize the cosmetic preparation escaping from the delivery container; and
    b5) an upstream storage container for the cosmetic preparation from which the cosmetic preparation can enter the delivery container through an access, wherein the pressure in the interior of the upstream storage container corresponds to the ambient pressure, wherein the upstream storage container has at least ten times the volume of the delivery container, and wherein the access between the upstream storage container and the delivery container includes a component for flow control configured to selectively interrupt flow of the cosmetic preparation from the upstream storage container into the delivery container.

2. The cosmetic product as claimed in claim 1, wherein the proportion by weight of the polar solvent a1) with respect to the total weight of the cosmetic preparation a) is about 55% to about 92% by weight.

3. The cosmetic product as claimed in claim 1, wherein the polar solvent a1) has a boiling point (20° C., 1013 mbar) between about 50° C. and about 110° C.

4. The cosmetic product as claimed in claim 1, wherein the polar solvent a1) is selected from the group of ethanol, isopropanol and water.

5. The cosmetic product as claimed in claim 1, wherein the proportion by weight of the copolymer a2) with respect to the total weight of the cosmetic preparation a) is about 1.0% to about 12% by weight.

6. The cosmetic product as claimed in claim 1, wherein the at least one copolymer comprises the monomers:
   i) N-tert-octylacrylamide,
   ii) acrylic acid,
   iii) tert-butylaminoethylmethacrylate;
   iv) methylmethacrylate; and
   v) hydroxypropylmethacrylate.

7. The cosmetic product as claimed in claim 1, wherein the at least one copolymer consists of the monomers:
   i) N-tert-octylacrylamide,
   ii) acrylic acid,
   iii) tert-butylaminoethylmethacrylate;
   iv) methylmethacrylate; and
   v) hydroxypropylmethacrylate.

8. The cosmetic product as claimed in claim 1, wherein the polar solvent a1) includes ethanol and water, and wherein the proportion by weight of water and ethanol with respect to the total weight of the polar solvent a1) is at least about 95% by weight.

9. The cosmetic product as claimed in claim 1, wherein the polar solvent a1) includes water, and wherein the proportion by weight of water with respect to the total weight of the polar solvent a1) is more than about 92% by weight.

10. The cosmetic product as claimed in claim 1, wherein the polar solvent a1) includes ethanol and water, and wherein the proportion by weight of ethanol with respect to the total weight of the cosmetic preparation is from about 40% to about 55% by weight.

11. The cosmetic product as claimed in claim 1, wherein the polar solvent a1) comprises ethanol and water, and wherein the ratio by weight of water to ethanol is from about 5:4 to about 4:5.

12. The cosmetic product as claimed in claim 1, wherein the proportion by weight of the copolymer a2) with respect to the total weight of the cosmetic preparation a) is from about 3.0% to about 9.0% by weight.

13. The cosmetic product as claimed in claim 1, wherein the cosmetic preparation a) contains, with respect to its total weight, from about 0.0005% to about 0.5% by weight of at least one poly-(C2-C3)alkylene glycol-modified silicone a3).

14. The cosmetic product as claimed in claim 13, wherein the poly-(C2-C3)alkylene glycol-modified silicone a3) is selected from the group formed by compounds with the INCI designation PEG-12 dimethicone.

15. The cosmetic product as claimed in claim 1, wherein the cosmetic preparation a) contains, with respect to its total weight, from about 0.5% to about 5.0% by weight of a film-forming polymer a4).

16. The cosmetic product as claimed in claim 15, wherein the film-forming polymer a4) is selected from the group formed by copolymers of acrylic acid and methacrylic acid.

17. The cosmetic product as claimed in claim 15, wherein the film-forming polymer a4) is selected from polyvinylpyrrolidones.

18. The cosmetic product as claimed in claim 15, wherein the film-forming polymer a4) is selected from the group formed by copolymers of methacryloylethyl-N,N-dimethylaminoxide.

19. The cosmetic product as claimed in claim 1, wherein the cosmetic preparation a) contains, with respect to its total weight, from about 0.2% to about 1.0% by weight of a nonionic surfactant a5), wherein the nonionic surfactant is selected from the group formed by PEG-40 Hydrogenated Castor Oil and PEG-40 Hydrogenated Castor Oil.

20. The cosmetic product as claimed in claim 1, wherein the cosmetic preparation a) contains, with respect to its total weight, from about 0.1% to about 0.8% % by weight of ester oil a6), wherein the ester oil a6) is an isopropylmyristate.

* * * * *